United States Patent [19]

Terry et al.

[11] Patent Number: 5,601,561
[45] Date of Patent: Feb. 11, 1997

[54] GUIDED BONE RASP

[75] Inventors: Glenn C. Terry, Seale, Ala.; Walter A. Thurber, Flagstaff, Ariz.

[73] Assignee: W. L. Gore & Associates, Inc., Newark, Del.

[21] Appl. No.: 373,663

[22] Filed: Jan. 17, 1995

[51] Int. Cl.⁶ .................................................. A61B 17/00
[52] U.S. Cl. ......................................................... 606/85
[58] Field of Search ........................... 606/60, 72, 80, 606/79, 85, 84, 86, 96

[56]  References Cited

U.S. PATENT DOCUMENTS

| | | |
|---|---|---|
| 5,234,435 | 8/1993 | Seagrave et al. . |
| 5,300,077 | 4/1994 | Howell . |
| 5,425,733 | 6/1995 | Schmieding .............................. 606/96 |

FOREIGN PATENT DOCUMENTS

| | | |
|---|---|---|
| 359883 | 3/1990 | European Pat. Off. . |
| 440991 | 8/1991 | European Pat. Off. . |
| 2636835 | 3/1990 | France . |

OTHER PUBLICATIONS

Advertisement for Gore Smoother™ Crucial Tool (W. L. Gore & Associates, Inc., Flagstaff, AZ).

*Primary Examiner*—Michael Powell Buiz
*Assistant Examiner*—Mark S. Leonardo
*Attorney, Agent, or Firm*—Wayne D. House

[57]  ABSTRACT

A surgical tool for use in preparing a graft path in anterior cruciate ligament reconstruction in a knee joint in which aligned tibial and femoral osseous tunnels are made for a bone-tendon-bone graft or similar surgery where two bone tunnels are in alignment. The tool comprises an elongated guide body having a guide shaft capable of being positioned within the tibial tunnel and extending into the femoral tunnel, and an elongated channel-like main body which is coaxial with the guide shaft. The main body includes a rasping head and is rotatably and axially slidable on the guide shaft for guided rasping of bone surfaces along the graft path. The rasp head fully encircles the guide shaft and is capable of following the guide shaft to enter and extend beyond the tibial tunnel. The leading end of the guide body includes a guide head with a flexible structure for connecting the head to the guide shaft. The guide head is movable through the tibial tunnel and into the femoral tunnel to position the guide shaft for subsequent rasping of surfaces along the graft path by manually moving the rasping head along and/or about the shaft. The flexible connection of the guide head to the guide shaft enables the knee to be flexed with the guide body is in place for inspection of the graft path in the area of the intercondylar notch while the rasping body may serve as a trial prosthesis to check for interference.

23 Claims, 6 Drawing Sheets

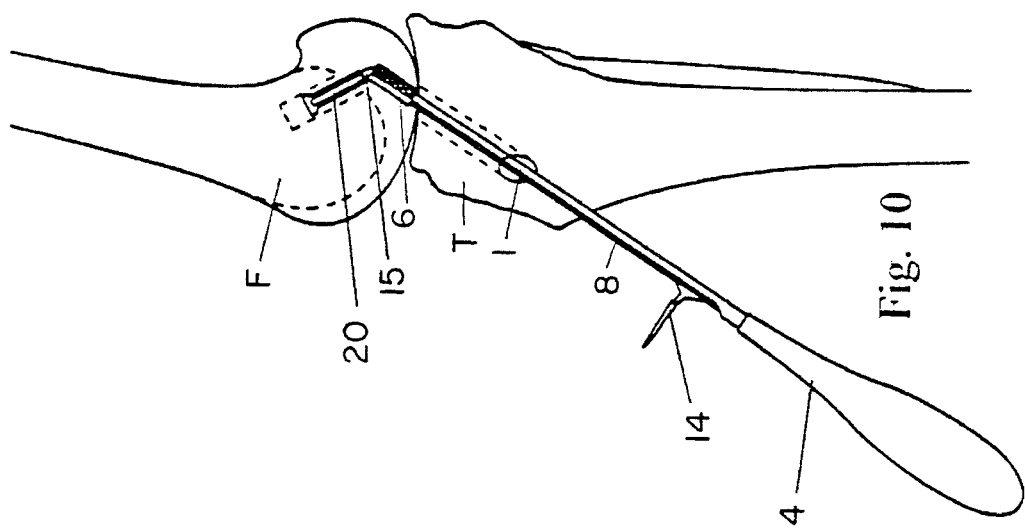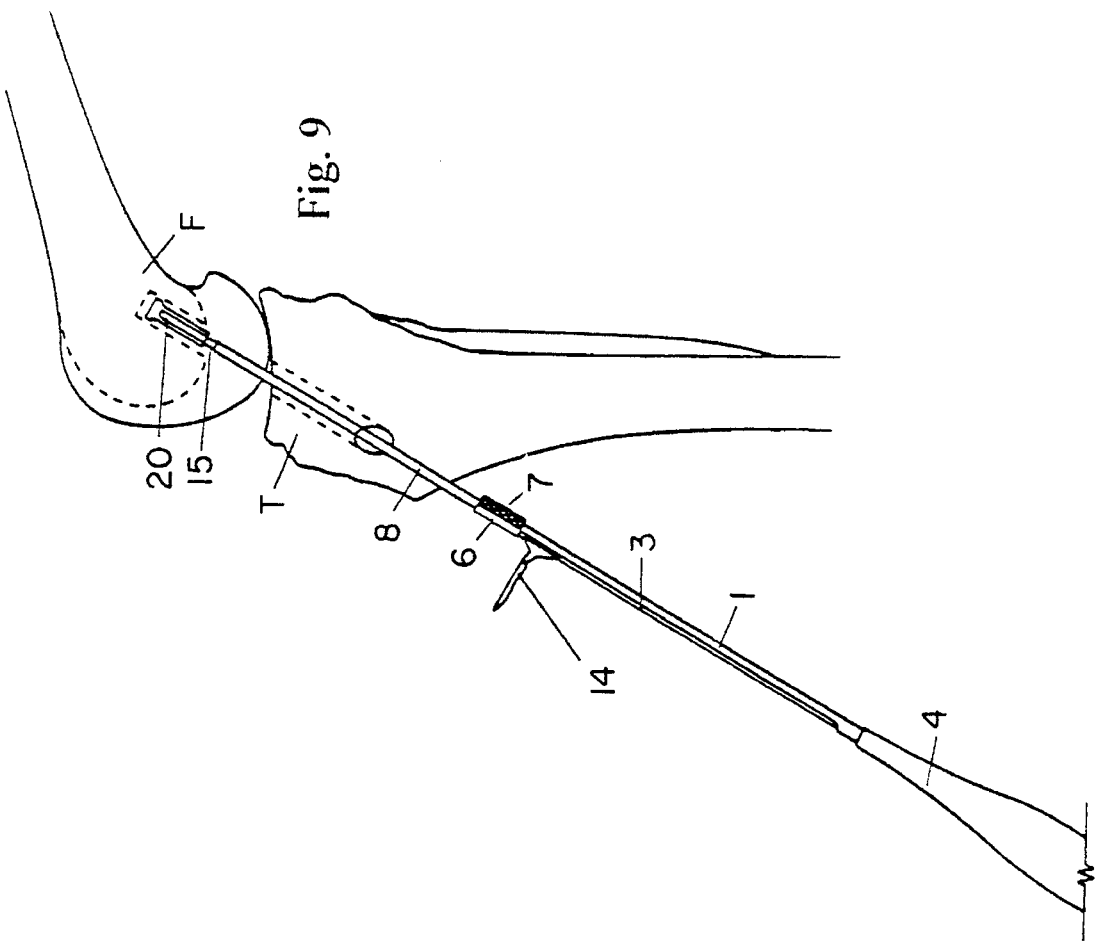

GUIDED BONE RASP

FIELD OF INVENTION

The present invention is in the field of orthopedic surgical tools.

BACKGROUND OF THE INVENTION

Surgical techniques for the reconstruction of the anterior cruciate ligament (ACL) within the knee joint have typically involved creating osseous tunnels open at each end in the tibia and femur. One end of a synthetic or natural graft is placed into and anchored in each respective tunnel with the graft in tension. The graft extending between the femur and tibia thus serves as a replacement for the ACL. Such a procedure has commonly involved surgical incisions both above and below the knee to provide access to the femoral and tibial tunnel openings. In such surgery a tool which has been commonly used is a device sold by W. L Gore & Associates and known by the trademark "GORE SMOOTHER CRUCIAL TOOL." This tool is a multi-function disposable instrument that serves:

1) as a trial prosthesis for assessment of the intercondylar notch, 2) to smooth the intercondylar notch and drill hole edges after drilling, 3) as a measurement gauge for proper selection of graft length, and 4) to engage and place a biologic or synthetic graft.

This prior art tool as shown in FIGS. 7 and 8 is comprised of a flexible main body 51 of silicone elastomer extruded onto stainless steel cable. The exterior surface of the silicone is then printed with measuring marks at 2 centimeter increments. A flexible braid 55 of stainless steel cable in an open pattern covers a major portion of the silicone. A relatively stiff stainless steel segment having an "eye" at its end and encased in polytetrafluoroethylene (PTFE) extends from one end of the main body and forms the leading end 52 of the tool. A flexible aramid fiber loop 53 extends from the other end of the main body as a trailing end of the tool. In use, the surgeon drills entry holes into the patient's tibia, below the joint, and femur, above the joint. The leading end of the tool is introduced into the tibial tunnel, across the knee joint space and into the femoral tunnel to exit laterally on the femur. At this point the trailing end of the tool will still protrude from the tibial tunnel. The main body of the tool is held in tension and slid back and forth through the bone tunnels so that the slightly abrasive surface of the open braid covering the main body may smooth the bone surfaces and edges along the path for the graft. The measuring marks assist in determining proper graft length. Once in place in the graft path the device functions as a trial prosthesis by allowing arthroscopic inspection for visual determination of whether the graft position will allow for free joint movement without impingement or interference between any tissue or bone. The flexible loop on the trailing end of the tool is attached to the ACL graft which is then pulled into position within the bone tunnels as the tool is removed through the femoral opening.

More recently, alternative endoscopic surgical techniques for the reconstruction of the anterior cruciate ligament (ACL) within the knee Joint have been developed so that the placement of a graft between the femur and tibia may be accomplished using a technique requiring only a single external skin incision. The graft is commonly one continuous piece of tissue taken from the patient's own knee and comprising sections or plugs of patella bone and tibial bone connected by a section of patellar tendon. Accordingly such a graft may be referred to as a "Bone-Patellar Tendon Bone" graft or simply as a "BPTB" graft.

In this more recent technique an open tibial tunnel is created to extend upwardly to exit the head of the tibia. This tibial tunnel is oriented so that a blind femoral tunnel may be bored using the tibial tunnel for access when the knee is flexed at, for example, approximately 60 to 80 degrees. Accordingly with the joint flexed, the femoral tunnel is in alignment with the tibial tunnel and creates an essentially straight path for placement of the graft. The obvious advantage to the patient of this improved technique is that it is less invasive since it can completely eliminate the need for an incision in the thigh and the additional trauma and morbidity which may be associated with that incision. However because the path of the graft does not involve two open ended osseous tunnels, the described flexible prior art tool of FIGS. 7–8 is not suitable for use with the improved technique.

The surgical procedure for ACL reconstruction for which the present invention is intended has been described by authors Douglas W. Jackson, MD; Robert Kenna; Timothy M. Simon, MS; and Peter Kurzweil, MD; in "Orthopedics" Volume 16, Number 9, (September 1993) under the title "Endoscopic ACL Reconstruction." The relevant portion of the described procedure is briefly summarized as follows:

Work within the joint itself is viewed arthroscopically and accomplished through anterolateral and anteromedial portals. The respective tunnels are bored in the tibia and femur, with the tibial tunnel exiting the tibial head in the area of the intercondylar eminence. A 2.4 mm eyeloop drill is drilled into place to be used as a guide for a cannulated reamer which creates the femoral osseous tunnel. The eyeloop drill may be drilled completely through the femur and out the anterolateral aspect of the thigh and be used later to pass sutures attached to the graft to pull and guide the graft into place. The blind femoral tunnel is bored beyond, and in alignment with, the tibial tunnel to a depth of approximately 25 mm, or slightly more than the length of the patellar bone plug, by a tool extending through the tibial tunnel with the knee flexed at approximately 70 degrees from the fully extended or "straight leg" orientation. The diameter of the femoral tunnel may initially be somewhat undersized in order to allow adjustment of the tunnel position after the initial drilling.

SUMMARY OF THE INVENTION

The present invention relates to a rasping tool to facilitate the preparation of bone surfaces, particularly those between osseous tunnels and in the area of the intercondylar notch, to create an acceptable path for placement of a graft using the single incision endoscopic technique. Typically, the femoral and tibial tunnels and a harvested bone-patellar tendon- bone graft are initially prepared so that the tunnels and respective bone plugs are precisely sized to match one another. However, while the tunnels themselves may be accurately drilled with the knee joint in one position, it may be necessary to accurately remove bone material from areas between the respective tunnels to insure that the graft path remains unobstructed during the range of motion of the knee joint.

In particular, the present tool provides a manual means of accurately removing and/or smoothing bone surfaces and edges to prepare a graft path to insure the graft is free of any impingement with bone and/or other tissue during movement of the knee joint through its full range of motion.

The tool itself comprises an external elongated semi-cylindrical or channel-shaped rigid main body of stainless steel which is coaxial with an internal elongated cylindrical rigid guide body shaft.

A guide head sized to fit accurately within a femoral tunnel is flexibly connected to the guide body shaft using a joint material of silicone covered stainless cable. The guide head can accordingly remain in place as the knee joint is flexed. Use of such a joint structure provides a number of desirable characteristics. The central wire gives the joint material the characteristic of being resilient and longitudinally non-extensible. While the joint is fully flexible and movable, it has a degree of "memory" which causes the guide head to tend to return to a position in which it aligned with respect to the guide shaft. This is particularly desirable to maintain alignment of the guide head with the guide shaft for initial insertion of the guide shaft and head through the tibial tunnel and into the femoral tunnel. Additionally, the covered cable (1) is flexible in any direction from its axis, (2) provides a flexible joint in a relatively short space, (3) provides a smooth exterior surface which does not tend to accumulate any tissue or debris, and (4) provides a smooth exterior surface which is readily cleaned and sterilized. The covered cable is also essentially sealed against any infiltration of debris or tissue which might create a binding effect or mechanically interfere with its movement or flexibility as could readily occur with a mechanically hinged joint.

The rasp body is provided with an abrasive or cutting surface over a portion of it exterior circumference. The tool allows accurately guided rotary and reciprocating manipulated operation of the rasp portion throughout a range of knee joint motion to facilitate preparation of the graft path within and between the osseous tunnels required when used in conjunction with single incision ACL reconstructive surgery where at least one of the osseous tunnels is blind or only open at one end.

The present invention provides numerous functions and benefits over prior tools:

1. The device serves as a trial prosthesis for assessment of the graft path in the area of the intercondylar notch.

2. The abrasive rasp surface on the guided head end of the main body may be used to smooth bone edges and surfaces along the graft path, and particularly within the intercondylar notch.

3. Markings may be placed on the guide body to serve as a measurement gauge for proper selection of graft length.

4. The movement of the rasp surface of the rasping head is guided for manual rotation and/or reciprocation by means positioned within a bone tunnel so that the rasping function can be more accurately controlled than is the case with cutting or abrading tools which are operated in a free-hand or unguided manner or which have abrading surfaces which are inherently flexible.

5. The precise control of the rasping function helps to minimize unnecessary removal of bone material.

6. In contrast to the described prior art tool, the exposure of the rasp surface portion of the cylindrical rasp head is circumferentially and axially limited to allow selective rasping action thereby minimizing the possibility of damage to bone or tissue which is not to be removed or smoothed.

DESCRIPTION OF THE DRAWINGS

FIG. 9 is a cross-sectional view of a flexed knee joint showing aligned bone tunnels with the guide body of the preferred embodiment in place and the rasp head retracted.

FIG. 10 is a cross-sectional view of a straightened knee joint showing the bone tunnels with the device of the preferred embodiment in place with the rasp head extended into the joint space.

DETAILED DESCRIPTION OF THE INVENTION

Figure 1:
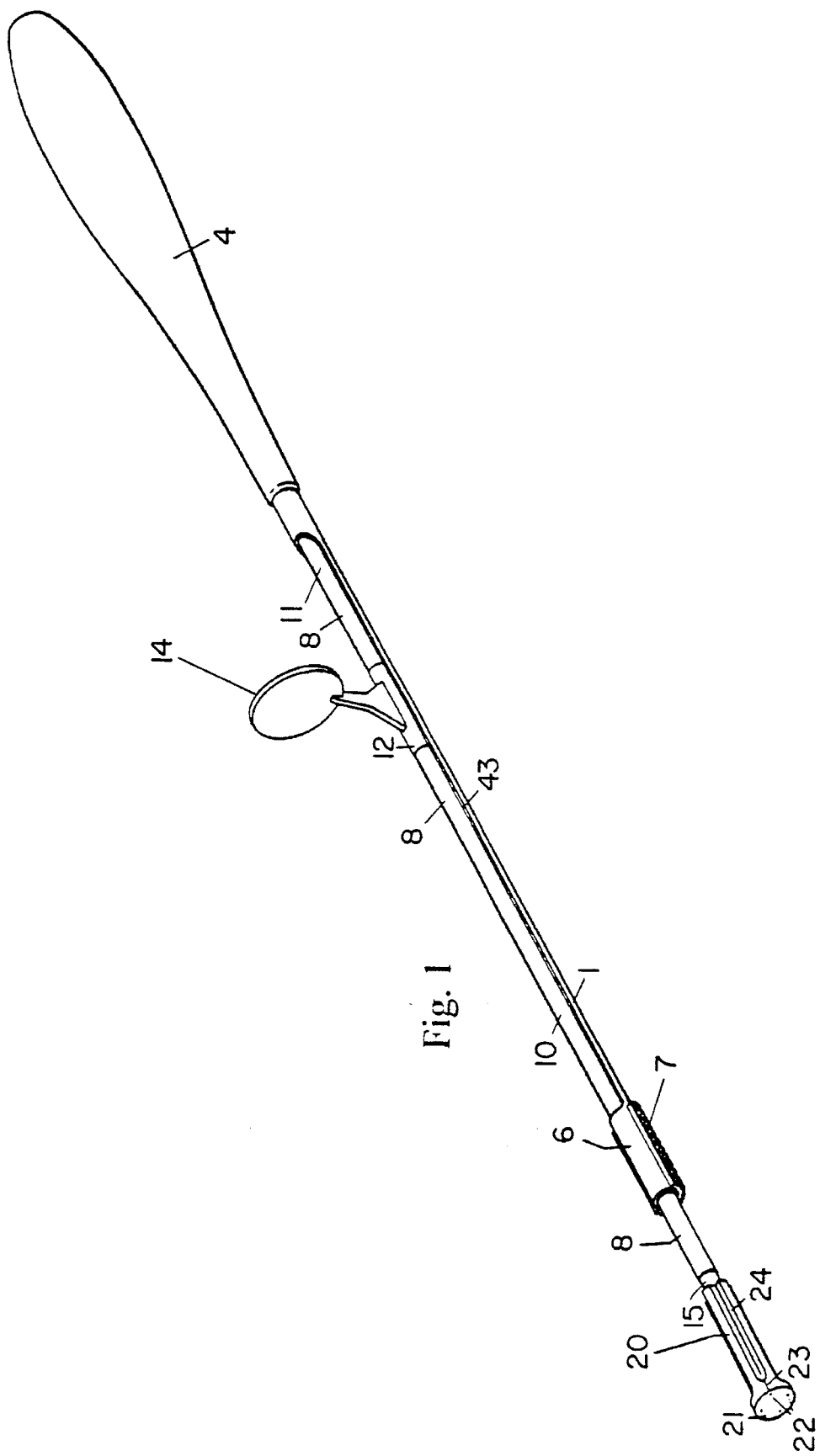
FIG. 1 is a perspective view of the assembled device of the preferred embodiment.
Figure 2:
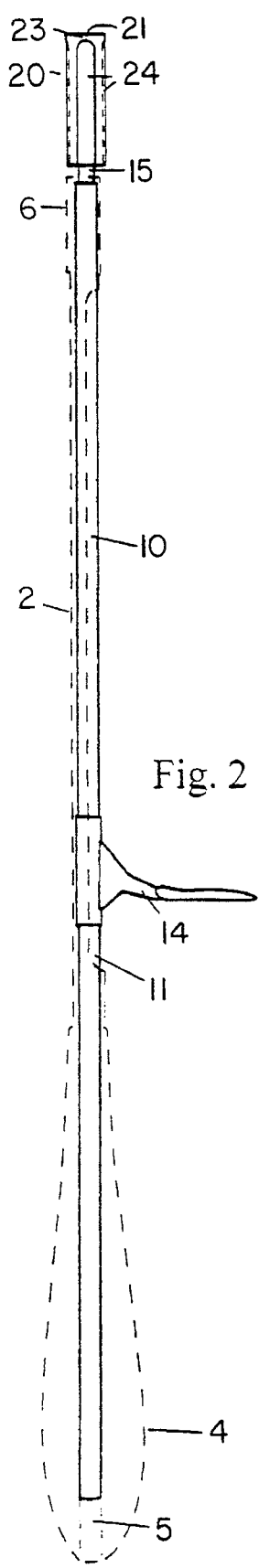
FIG. 2 is a plan view of the guide body of the preferred shown in place within the main body.
Figure 3:
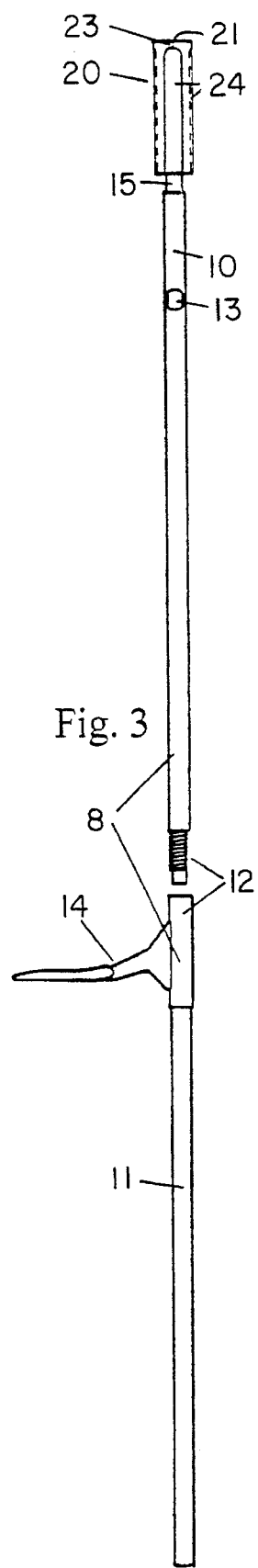
FIG. 3 is a plan view of the leading and trailing portions of the guide shaft of the preferred embodiment.
Figure 4:
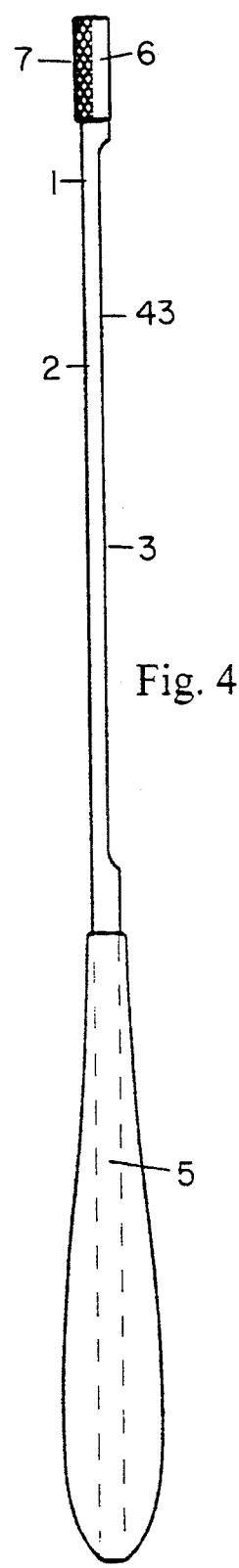
FIG. 4 is a plan view of the main body of the preferred embodiment.
Figure 5:
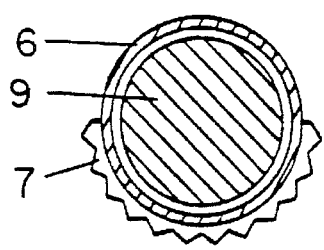
FIG. 5 is a cross-section of the guide shaft and rasp head of the main body taken at A—A of FIG. 1.

The tool of the present invention comprises a main body 1 of stainless steel about 10.75 in. (273 mm) in length having a center or intermediate portion 2 of an elongated hollow semi-cylindrical cross section approximately 5.5 in. (104 mm) in length and 0.275 in. (7 mm) in outside diameter forming an open-sided guide channel 3 which mates with a coaxial guide shaft assembly 8. Rigidly fixed to one end of the center portion 2 of the body is a hollow cylindrical rasp head portion 6 about 0.75 in. (19 mm) in length with a diameter of approximately 0.4 in. (10 mm). The rasp head 6 is provided with an abrasive or rasp-like exterior 7 over about half of its circumference or an essentially semicylindrical portion of its surface. As illustrated in the figures, the semicylindrical rasp surface will typically be oriented with respect to the rasp body to encircle a portion of the circumference of the rasp body corresponding to that portion encircled and defined by the semicylindrical guide channel 3. The rasp surface may be a machined, knurled or textured area to provide a toothed, file-like surface with an abrasive or cutting ability sufficient for removing bone. Alternatively the rasp surface may be essentially abrasive and created using recognized methods of permanently attaching diamond dust or other suitable abrasive to the rasp head surface.

At an opposite end of the central portion of the main body a handle portion 4 provides a comfortable means of manually grasping and manipulating the rasping portion of the tool device. The handle is preferably provided with a longitudinal full-length cylindrical bore 5 of the same inner diameter as the guide channel 3 and which exits at the base of the handle 4 and which creates an extension of the guide channel 3. This central bore 5 is open at each end to facilitate cleaning and sterilization of the device.

The guide body assembly is comprised of a guide head 20 flexibly attached to a leading end of a guide shaft 8 having aligned coaxial leading shaft portion 10 and trailing shaft portion 11 of tubular stainless steel which are coupled together end-to-end using a common male/female threaded connection 12 or other suitable detachable joint structure in the assembled device. To facilitate assembly or disassembly of the threaded guide shaft connection, one or both of the two shaft portions 10 and 11 is provided with a short area 13 upon its exterior surface having two opposite flattened parallel faces as means for engagement with a wrench or similar tool to allow application of sufficient torque to securely tighten or loosen the threaded joint 12.

Figure 13:
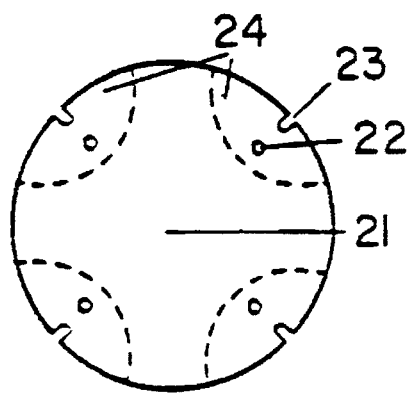
FIG. 13 is a plan view of the end surface of the guide of the preferred embodiment showing apertures for affixing sutures.

The trailing shaft portion 11 of the guide body assembly is approximately 5.125 in. (130 mm) in length and is provided with a rigidly secured manually engageable thumb or finger brace 14 extending generally perpendicular to the shaft axis near the joint end of this shaft portion and providing a broad flat planar surface against which a thumb or finger may rest. The guide head 20 is a rigid, generally cylindrical structure of suitable material, such as stainless steel, approximately 1 in. (25 mm) in length and 0.3 in. (8 mm) in diameter or of a size and/or shape which will correspond closely to the length and diameter of the prepared femoral tunnel. The transverse surface or end face 21 of the tip of the head is generally flat and circular to seat against the transverse end of a femoral tunnel. The sides of the head may be partially cut away or longitudinally grooved except at its tip or circular end face 21. As can be seen in FIG. 13 the tip is provided with one or more pairs of an aperture 22 and a notch 23 extending through the tip to one of the grooves 24 to allow tying or affixing suture material to the guide head to provide a means of (1) pulling the head of the guide body assembly of the device into position in the femoral tunnel, or (2) securing the guide body assembly of the device once it is in position. A suture or similar thread-like material for this purpose can be drawn into the tibial and femoral tunnels using the thin elongated eye-loop drill which also serves as an axial guide for a tubular or cannulated reamer used in drilling the femoral tunnel. The eyeloop drill is externally accessible when it is drilled completely through the femur and out the anterolateral aspect of the thigh and through the skin.

The guide head 20 is joined to the guide body by means of a short length of flexible and durable joint material 15 such as a sleeve of silicone elastomer 16 or similar smooth-surfaced flexible plastic material extruded onto a flexible stainless steel cable 17 and having a diameter of approximately 0.15 in. (4 mm).

Figure 12:
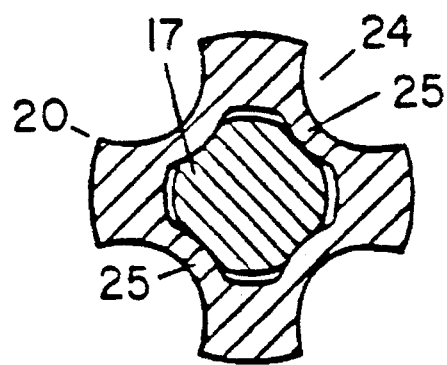
FIG. 12 is view similar to FIG. 11, showing the radial crimping of the guide head.

While the joint material may be adhered into the guide head and the leading end of the leading shaft portion of the guide body using a suitable adhesive, such as a settable or curable silicone, it may be desirable to use recognized inert materials and strictly mechanical methods of securing these respective elements together to minimize problems which may be inherent in the use of the tool as a surgical instrument. Of primary concern are minimizing any potential adverse reaction to foreign materials introduced even temporarily into a patient's body, and insurance of the structural integrity of the device during surgical use. The avoidance of chemical adhesives may help minimize any possibility of a patient's adverse reaction to such chemicals. Since the device is intended for reuse, a mechanical joint is also likely to be more tolerant to repeated cleaning and heat sterilization of the device. Accordingly, in order to insure a secure mechanical attachment of the joint material into the guide head the joint material may be crimped in place. An appropriate method of such crimping is illustrated in the cross section shown in FIG. 12. The longitudinal flutes or grooves 24 in the outer cylindrical surface of the guide head 20 result in thinner walls 25 in the areas of the flutes and thereby allowing greater deformability of the walls of the head, which are forced inwardly about the core cable 17 of the joint material 16 as the walls 25 are compressed radially inward.

Figure 6A:
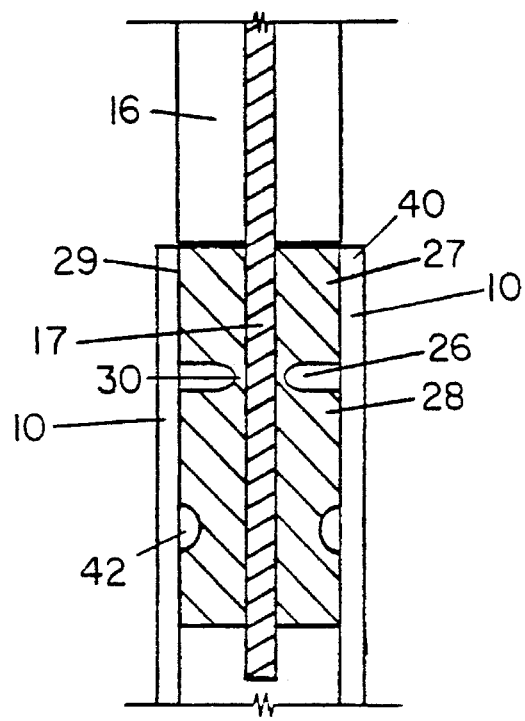
FIG. 6a is a partial cross-section of the end of the guide shaft and flexible joint taken at B—B of FIG. 1 showing a ferrule used to attach the flexible joint material into the shaft prior to longitudinal crimping of the ferrule.
Figure 6B:
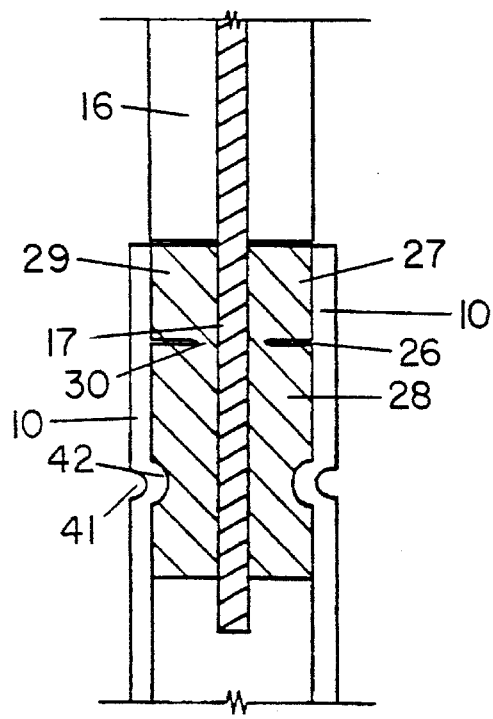
FIG. 6b is a partial cross-section similar to FIG. 6a showing a ferrule crimped onto the joint cable and crimped into the guide shaft.
Figure 7:
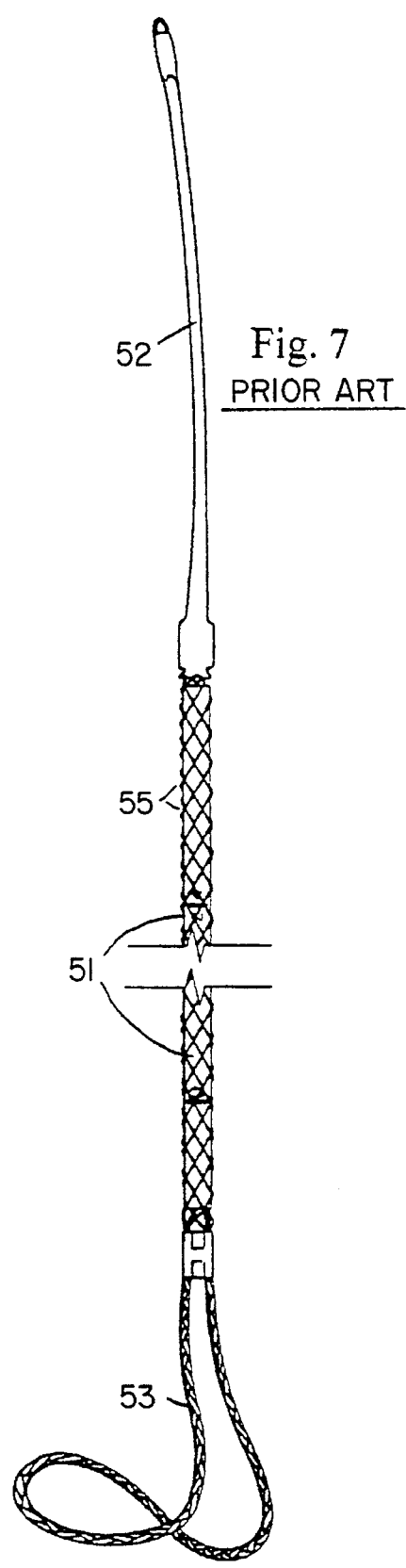
FIG. 7 is a plan view of a prior art device.
Figure 8:
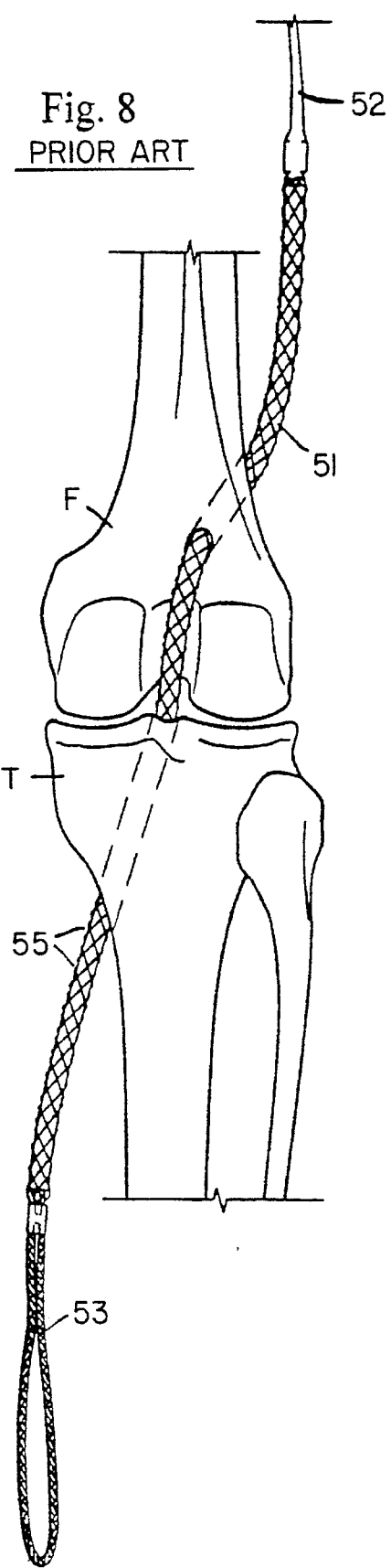
FIG. 8 is a perspective view of a prior art device in place within the bone tunnels.
Figure 11:
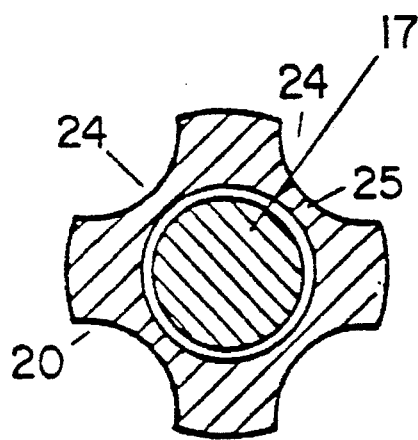
FIG. 11 is a cross-section of the guide head of the device of the preferred embodiment taken at C—C of FIG. 1 showing the guide head prior to crimping.

Secure attachment of the flexible joint material into the leading end of the guide shaft may be accomplished, by first securing the joint material into a stainless steel ferrule 29 using a novel longitudinal crimping of the ferrule. A portion of the silicone covering sleeve 16 is removed to expose a portion of the core cable 17 to be inserted into the ferrule. To allow the crimped ferrule to maintain a rigid cylindrical outer surface which will fit snugly into the hollow end of the guide shaft, it is desirable to avoid distorting the circular cross section of the ferrule as might occur if the ferrule 29 were to be compressed merely radially to, for example, form an annular impression to crimp it in place onto the joint material. The crimping function of the ferrule in the present invention is therefore accomplished by providing the ferrule with one or more crimp structures comprising an annular groove 26 separating two barrel-like sections 27 and 28 of the ferrule body. As shown in FIG. 6b, as these two body sections 27 and 28 are pressed axially toward one another and into engagement, the groove 26 is closed and the ferrule material 30 between the respective body sections is distorted and displaced radially inwardly to tighten about the core wire of the joint material and anchor the ferrule. Thus, the ferrule 29 is crimped in place without any significant diametric change or distortion of its external cylindrical shape. The ferrule with the cable crimped therein is then placed into the tubular leading end portion 40 of the guide shaft 10 and secured using one or more annular grooves 41 pressed or knurled into the exterior of the wall of the guide shaft end portion to deform an annular portion of the wall inwardly to positively engage a corresponding annular groove 42 in the exterior of the ferrule. The ferrule groove may be preformed or formed during the crimping of the tubular shaft onto the ferrule.

While the described structures for attaching the ends of the joint material to the respective portions of the guide body assembly are mechanically sound, there are medical concerns stemming from the reusability of the device which may also be taken into account. Accordingly, it may be desirable to provide a slight cylindrical recess within the joint end of guide head 20 and ferrule 29 where such recess is sized to accommodate and seal snugly around the circumference of an end of the silicone covering 16 of the joint material so as to minimize or eliminate surface gaps, or similar areas which might trap or accumulate tissue or debris as the joint material flexes.

The tool is assembled by placing the trailing portion 11 of the guide shaft into the guide channel 3 of the main body with the internally threaded joint connection end toward the rasp head. The externally threaded joint connection end of the guide shaft is inserted longitudinally into the guide channel though the hollow rasp head to meet with the joint end of the trailing portion of the guide shaft and the guide shaft portions are threaded together to form the complete guide shaft.

Once the device is assembled as described with the respective guide shaft portions threaded together, the guide shaft assembly cannot be removed from the main body without first disengaging the guide shaft sections. The tool is disassembled into three primary parts for cleaning and sterilization by merely reversing the assembly sequence.

Figure 14:
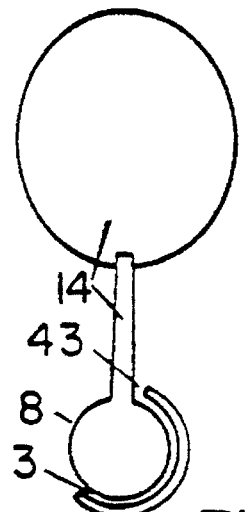
FIG. 14 is a cross-section of the guide shaft and main body taken through the thumb brace and corresponding to D—D of FIG. 1, showing one extreme position of the relative rotation between the main body and guide shaft.
Figure 15:
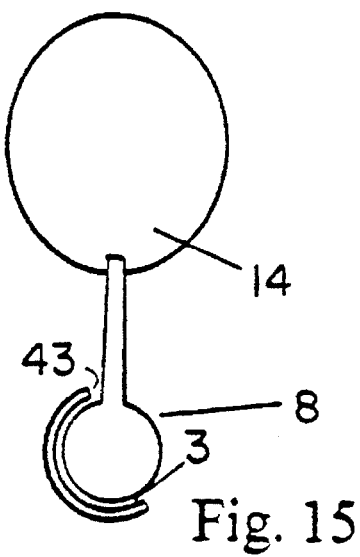
FIG. 15 is a view similar to FIG. 14 showing an opposite extreme of relative rotation between the main body and guide shaft.

The tool is used following the drilling of the respective tibial and femoral osseous tunnels. As shown in FIG. 9, with the knee joint initially flexed so as to align the respective bone tunnels and with the guide head oriented to be essentially coaxial with the guide shaft, the guide shaft of the assembled tool is fully axially extended beyond the rasping head and may be inserted head first into the tunnel within the tibia T, across the joint space and into the tunnel within the femur F, using the finger brace 14. Alternatively the guide head may be secured, using sutures attached through holes 22, to the trailing end of a guide wire or drill guide and pulled into place. The guide head thus becomes seated within the femoral tunnel while the flexible joint of the guide body is positioned generally within the joint space and the guide shaft is positioned generally within the tibial tunnel and extending at least partially into the joint space. At this point the rasping head 6 around the guide shaft is still outside the tibial tunnel as seen in FIG. 9. The flexibility of joint between guide head and guide shaft allows these parts of the device to remain in position during virtually any flexion of the knee joint. As the knee is moved through a range of motion, the joint can be visually inspected for any material which might cause interference or impingement within or along the graft path. The main body 1 can be longitudinally slid or rotated upon the guiding shaft 8 to selectively and accurately abrade or cut bone material and thereby appropriately shape and smooth the bone surfaces and edges along the graft path. As shown in FIGS. 14 and 15, the main body can be rotated about the guide shaft through an angle of nearly 180 degrees with the rotational movement being blocked at each end of the such rotation by an edge 43 of the semicylindrical guide channel 3 coming into contact with the base of the thumb brace 14.

While all or a portion of the cylindrical surface of the rasp head may be provided with a rasp surface, it will generally be desirable to limit the rasp surface to, for example, a semicylindrical surface so that the rasping action may be confined to chosen areas in order to prevent damage to bone or tissue, such as existing ligaments, which might otherwise be likely to inadvertently come into contact with a portion of the rasp surface. However even with the rasp surface covering only approximately 180 degrees of the cylindrical surface of the rasp head, the guide shaft assembly carrying the main body may be rotated so that at least a portion of the rasp surface may be selectively engaged with a portion of nearly the entire circumferential area surrounding the tool. This circumferential area would correspond, for example, to the full outer surface of a bone-tendon-bone graft.

Other variations within the scope of this invention will be apparent from the described embodiment and it is intended that the present descriptions be illustrative of the inventive features encompassed by the appended claims.

What is claimed is:

1. A surgical tool for preparation of a graft path wherein the graft path includes a first and a second tunnel in bone, said tool comprising an elongated guide body capable of extending through said first tunnel and being positioned within said second tunnel, and an elongated rasping body having a rasping portion capable of entering and extending beyond a first tunnel for rasping a surface along said graft path, said rasping portion being coaxial with said guide body portion and guided by said guide body portion for rotational and axial movement relative to the guide body portion along the graft path.

2. A surgical tool according to claim 1 wherein said portion of one of said bodies is a shaft to be positioned centrally of one of said tunnels and said portion of the other body has means engaging the outer surface of said shaft to guide said portions for relative axial and rotational movement.

3. A surgical tool according to claim 2 wherein each of said bodies has a manually engageable extension part to manually vary the orientation of the respective body portion.

4. A surgical tool according to claim 3 wherein said guide body portion comprises said shaft.

5. A surgical tool according to claim 4 wherein said rasping body comprises a cylindrical rasping head encircling said shaft.

6. A surgical tool according to claim 5 wherein said elongated rasping body comprises an elongated channel-shaped structure having an open side and wherein said elongated channel-shaped structure is coaxial with and slidable on said shaft.

7. A surgical tool according to claim 6 wherein said shaft has a manually engageable member extending transversely relative to the shaft and outwardly through the open side of the elongated channel-shaped structure for adjustably positioning the shaft along the graft path.

8. A surgical tool according to claim 5 wherein said cylindrical rasping head has a rasping surface extending over less than the entire circumference of the head to enable selective rasping at only a side of the graft path where the rasping surface is located.

9. A surgical tool according to claim 5 for use in anterior cruciate ligament reconstruction in a knee joint in which the graft path comprises tibial and femoral osseous tunnels and wherein said elongated guide body comprises a head member with means for flexibly connecting said head member to a leading end of the shaft.

10. A surgical tool according to claim 9 wherein said head member is movable through the tibial tunnel and into the femoral tunnel to position said shaft for subsequent rasping of a surface along said graft path by manually moving said rasping head relative to said shaft.

11. A surgical tool according to claim 10 wherein said head member comprises pulling means for allowing said head member to be pulled into at least one of said tunnels.

12. A surgical tool according to claim 11 wherein said pulling means comprises means for the attachment of suture material to said head member.

13. A surgical tool according to claim 12 wherein said suture attachment means comprises one or more apertures through a portion of said head member.

14. A surgical tool according to claim 10 wherein said means for connecting the guide body head member to said shaft comprises a flexible structure enabling the knee to be flexed for inspection of the intercondylar notch while the guide body is in place with the guide body head member in the femoral tunnel and with the rasp body serving as a trial prosthesis.

15. A surgical tool according to claim 14 wherein said means for flexibly connecting the guide body head member to said shaft comprises a cable, and includes a first means for attaching said head member to the cable and a second means for attaching said shaft to the cable.

16. A surgical tool according to claim 15 wherein said cable has an exposed section between said shaft and said guide body head member, said exposed section comprising a smooth-surfaced cover completely enclosing a flexible metal portion of the cable.

17. A surgical tool according to claim 15 wherein one of said first and second means comprises a ferrule crimped on said cable, said ferrule having two coaxial barrel portions with similar coaxial cylindrical inner surface portions forming portions of a cable passage, said barrel portions being interconnected by an integral deformed annular ferrule section having an inner wall surface crimped into engagement with the cable by axial movement of said barrel portions toward each other by application of external forces thereto to cause said deformed ferrule section to be displaced radially inwardly and crimped against the cable without any change in the external configuration of other parts of the barrel portions.

18. A surgical tool for use in preparing a graft path in anterior cruciate ligament reconstruction in a knee joint in which aligned tibial and femoral osseous tunnels are made for a bone-tendon-bone graft, said tool comprising an elongated guide body having a portion capable of being positioned within the tibial tunnel and an elongated rasping body having a rasping portion capable of entering and extending beyond the tibial tunnel for rasping surface areas along the graft path, said rasping portion being coaxial with said guide body portion and guided by said guide body portion for rotational and axial movement relative to the guide body portion along the graft path, said guide body comprising a shaft, said rasping body portion comprising a cylindrical rasping head encircling and slidable on said shaft, said guide body comprising a head member with means for connecting said head member to a leading end of the shaft, said head member being movable through the tibial tunnel and into the femoral tunnel to position said shaft for subsequent rasping of surfaces along said graft path by manually moving said rasping head relative to said shaft.

19. A surgical tool in accordance with claim 18 including manually engageable means for rotatably and reciprocally operating said rasping head on said shaft.

20. A surgical tool in accordance with claim 18 including manually engageable means for adjusting the position of the shaft.

21. A surgical tool in accordance with claim 20 wherein said rasping body portion comprises an elongated open-sided channel-shaped structure coaxial with and slidable on said shaft, and said manually engageable means for adjusting the position of the shaft comprises a manually engageable member extending transversely relative to the shaft and outwardly through the open side of the channel-shaped structure.

22. A surgical tool in accordance with claim 21 wherein said rasping head has a rasping surface extending over less than the entire circumference of the head to enable selective rasping at only a side of the graft path where the rasping surface is located.

23. A surgical tool according to claim 18 wherein said means for connecting the guide body head member to said shaft comprises a flexible structure enabling the knee to be flexed for inspection of the intercondylar notch while the guide body is in place with the guide body head member in the femoral tunnel and with the rasping body serving as a trial prosthesis.

* * * * *